United States Patent [19]

Fujiyama et al.

[11] Patent Number: 4,575,551

[45] Date of Patent: Mar. 11, 1986

[54] ACIDIC HETEROPOLYSACCHARIDE AM-2

[75] Inventors: Seiichi Fujiyama; Hiroyuki Minakami; Kenji Tayama; Hiroshi Masai, all of Aichi, Japan

[73] Assignee: Nakano Vinegar Co., Ltd., Handa, Japan

[21] Appl. No.: 545,270

[22] Filed: Oct. 25, 1983

[30] Foreign Application Priority Data

May 2, 1983 [JP] Japan ................. 58-076265

[51] Int. Cl.$^4$ .......... C12P 19/06; C12P 1/16; C08B 37/00
[52] U.S. Cl. ................. 536/123; 426/583; 426/605; 435/101; 435/253; 536/1.1; 536/114
[58] Field of Search ............ 536/1.1, 114, 123

[56] References Cited

U.S. PATENT DOCUMENTS

| | | | |
|---|---|---|---|
| 4,331,440 | 5/1982 | Racciato | 536/123 |
| 4,342,866 | 8/1982 | Kang et al. | 536/123 |
| 4,454,316 | 6/1984 | Veeder et al. | 536/123 |

FOREIGN PATENT DOCUMENTS 2058106 of 1979 United Kingdom ........... 536/123
2058107 of 1979 United Kingdom ........... 536/123

OTHER PUBLICATIONS

The Biological Synthesis of Dextran from Dextrins, Edward J. Hehre, Mar. 5, 1951, pp. 161–174.
Isolation and Characterization of a New Extracellular Polysaccharide from a Cellulose–Negative Strain of Acetobacterxylinum, Valla et al., Can. J. Microbiol., vol. 27, 1981, pp. 599–603.
Synthesis of Cellulose by Acetobacterxylinum, Hestrin et al., vol. 58, pp. 345–352, 1954.
Sintez, Polysakharidov Ursusokisiymi Bacteriami M. S. Loytsyanskaya, Trudy Petergovskogo Biologich Eskogo Instituta L6U, #19, 1965, pp. 20–28.

*Primary Examiner*—Johnnie R. Brown
*Attorney, Agent, or Firm*—Browdy and Neimark

[57] ABSTRACT

Novel highly viscous acidic heterpolysaccharide AM-2 is produced from a strain of genus Acetobacter isolated from vinegar mash, and is useful as an adhesive, coating agent, drilling mud additive, enhanced oil recovering agent, etc., as well as a material useful for the production of foods, drugs and cosmetics because of its safety and high viscosity.

1 Claim, 7 Drawing Figures

4,575,551

ACIDIC HETEROPOLYSACCHARIDE AM-2

FIELD OF THE INVENTION

The present invention relates to the novel acidic heteropolysaccharide AM-2 and a process for the production thereof.

BACKGROUND OF THE INVENTION

Heretofore, viscous polysaccharides have been widely used for their properties of thickness and viscosity as additives for foods and cosmetics. Utilities as an adhesive, coating agent, freezing stabilizer, lubricating agent, additive for drilling mud, enhanced oil recovering agent, etc., have also been developed. Recently, it has been found that certain polysaccharides have pharmacological activity, such as anti-tumor activity, hypotensive activity, etc. Therefore, an increase of their use as drugs is expected.

It is well known that certain microorganisms produce polysaccharides. For example, strains of genera Alcaligenes, Bacillus, Xanthomonas, Arthrobacter, Azotobacter, Pseudomonas, Leuconostoc, Aureobasidium, etc., produce polysaccharides.

Further, it is also known that certain strains of genus Acetobacter produce polysaccharides, for example, cellulose from *Acetobacter xylinum* (Biochem.J., 58, 345 (1954)), levan from *Acetobacter suboxydans* (Tr. Petergof. Biol. Inst. Leningrad. Gos. Univ., 19, 20 (1965)), and dextran from *Acetobacter capsulatum* (J. Biol. Chem., 192, 161 (1951)). It was also reported that a nitrogen-containing polysaccharide composed of glucose, mannose, rhamnose and glucuronic acid was isolated from a spontaneous mutant of *Acetobacter xylinum* (Can. J. Microbiol., 27, 599 (1981)).

SUMMARY OF THE INVENTION

In the course of their search for the production of a highly viscous, non-toxic polysaccharide, the present inventors have screened microorganisms participating in the brewing of various fermentation foods. It has been found that a strain of genus Acetobacter isolated from vinegar mash produces a novel acidic heteropolysaccharide. Acetic acid bacteria have been used from prehistoric times for the production of vinegar and their safety has been confirmed. The present invention is based on this finding.

It was reported that *Acetobacter xylinum* produced the acidic heteropolysaccharide composed of glucose, rhamnose, mannose and glucuronic acid in a molar ratio of 3:1:1:1, respectively (Can. J. Microbiol., 27, 599 (1981)) and that this purified acidic heteropolysaccharide contained nitrogen in an amount corresponding to a protein content of 1.4% (by weight). On the other hand, the polysaccharide of the present invention contains acetyl groups in addition to glucose, mannose, rhamnose and glucuronic acid. Further, the molar ratio of glucose, mannose, rhamnose and glucuronic acid is 4:0.9~1.1:0.9~1.1:0.9~1.1, respectively, and contains no nitrogen. Thus, the polysaccharide of the present invention is evidently different from the acidic heteropolysaccharide produced by *Acetobacter xylinum* in their constitutional components and their proportions.

Accordingly, the acidic heteropolysaccharide of the present invention has been identified to be a novel polysaccharide and named acidic heteropolysaccharide AM-2.

DETAILED DESCRIPTION OF THE INVENTION

The physical and chemical properties of the acidic heteropolysaccharide AM-2 of the present invention, referred to as AM-2 hereinafter, are as follows:

1. Glucose, rhamnose, mannose and glucuronic acid were detected in AM-2 by the method which comprises hydrolyzing AM-2 with 2N-trifluoroacetic acid at 100° C. for 18 hours, subjecting the product to thin-layer chromatography using a mobile phase of acetone-isopropanol-0.1M lactic acid (2:2:1), and then coloring with a reagent consisting of aniline, diphenylamine, acetone and phosphoric acid. Further analysis of AM-2 by gas chromatography shows that at least glucose, rhamnose, mannose and glucuronic acid are the main constitutional saccharides of AM-2, and the molar ratio is 4:0.9~1.1:0.9~1.1:0.9~1.1, respectively.

The $^{13}$C-nuclear magnetic resonance spectrum of AM-2 shows a peak at 21.2 ppm, indicating the presence of acetyl groups. It has been found that the acetyl group content is 4 to 8% by colorimetric determination using hydroxylamine and also by determination of acetic acid liberated from AM-2 by an alkaline treatment.

When cetyltrimethylammonium bromide or cetylpyridinium chloride is added to AM-2, a white precipitate is formed. Thus, AM-2 is acidic.

Figure 1:
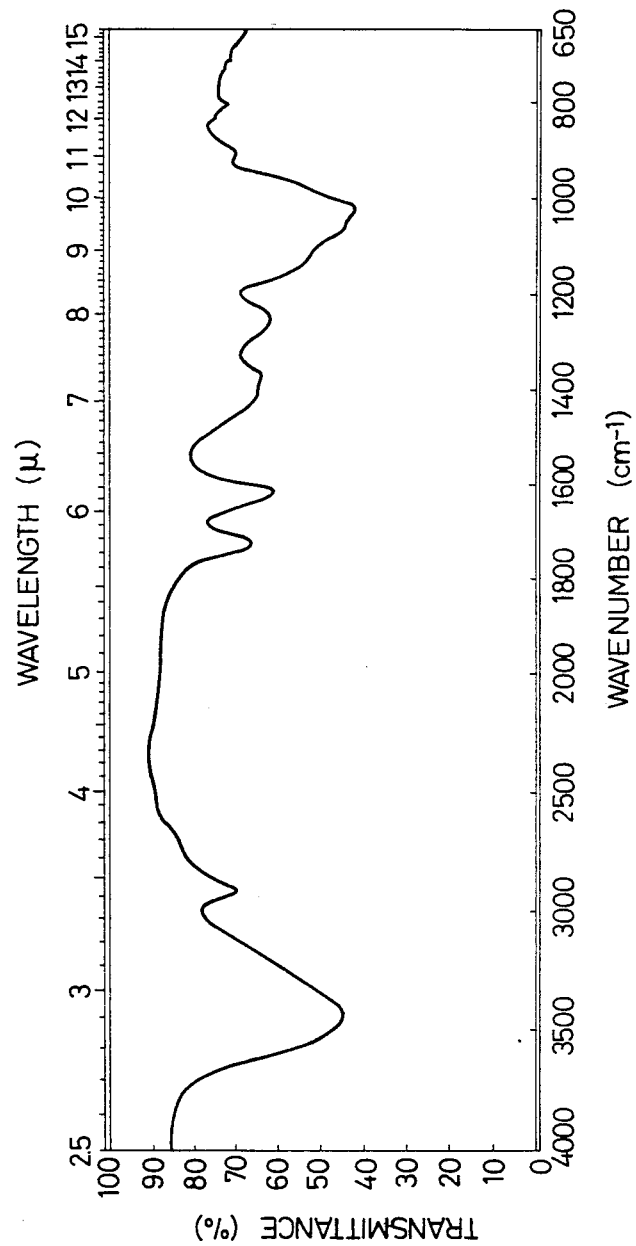
FIG. 1 shows the infrared spectrum of AM-2 of the present invention.

2. The infrared spectrum is shown in FIG. 1.

3. Color reactions:
Anthrone reaction: positive
Carbazole reaction: positive
Elson-Morgan's reaction: negative
Iodine reaction: positive 4. Solubility in solvents
Soluble in water and insoluble in ethanol, ether, acetone, etc.

5. Color and form
The purified AM-2 is white, and cotton-like or fibrous form.

6. Viscosity
The aqueous solution of AM-2 is colorless, transparent and viscous. The viscosity of a 1% aqueous solution is 1200 to 2000 cps as determined with a Brookfield viscometer, i.e., a torque measuring viscometer, (manufactured by Tokyo Keiki Co., Ltd.) at 25° C. and a rate of 30 rpm.

Figure 2:
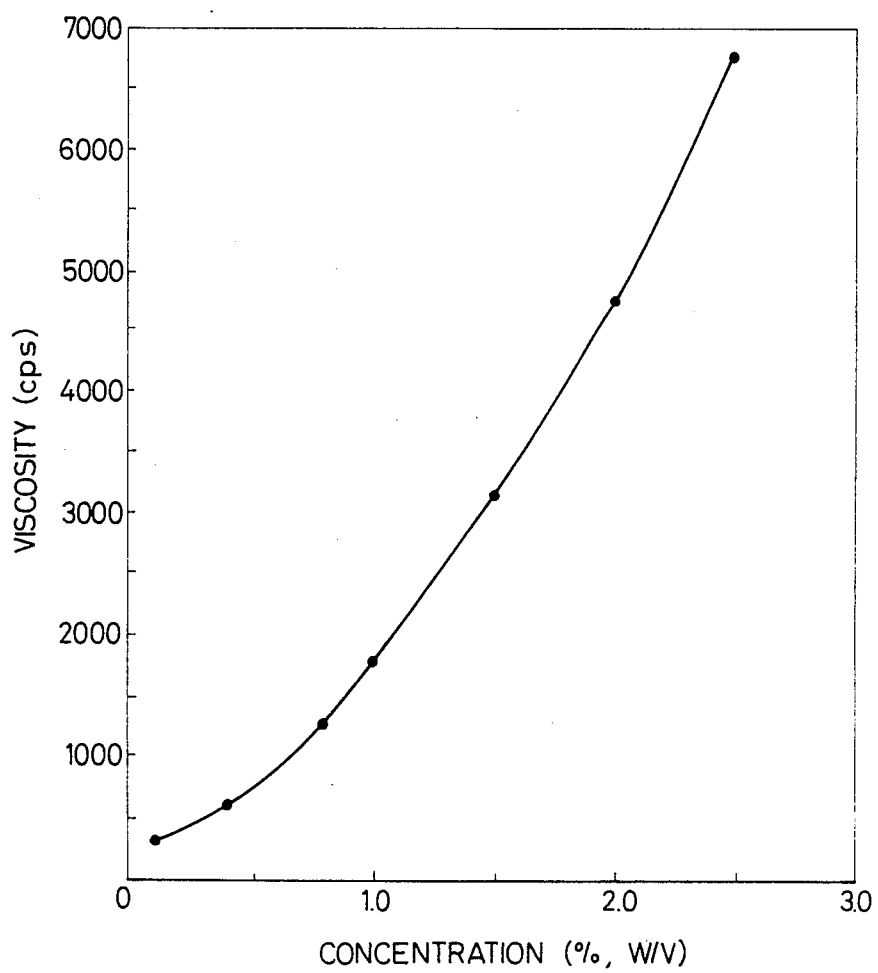
FIG. 2 is a graph showing the relationship between the viscosity and concentration of AM-2 of the present invention.
Figure 3:
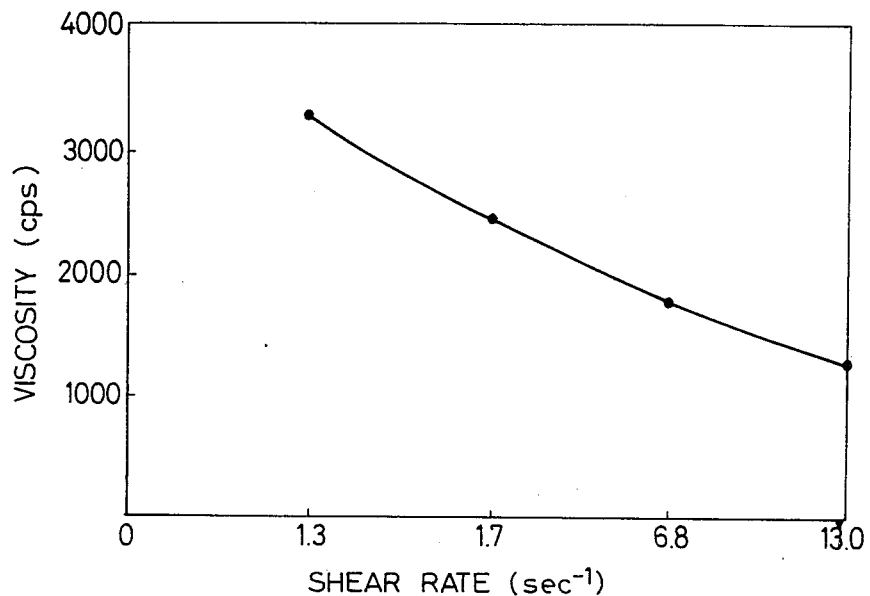
FIG. 3 is a graph showing the relationship between the viscosity and shear rate (in $\sec^{-1}$) of 1.0% aqueous solution of AM-2.

The relationship between the concentration of AM-2 and the viscosity of the solution is shown in FIG. 2. The effect of shear rate on the viscosity of 1% (w/v) aqueous solution is shown in FIG. 3.

Figure 4:
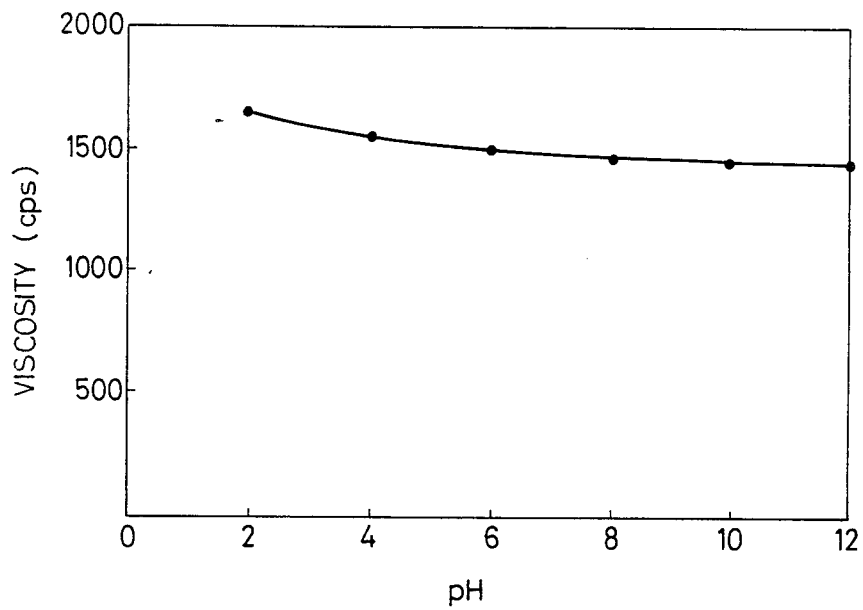
FIG. 4 is a graph showing the relationship between the viscosity and pH of 1% aqueous solution of AM-2.

The effect of pH on the viscosity of the 1% (w/v) aqueous solution is shown in FIG. 4. No changes in viscosity are observed upon variation of the pH.

Figure 5:
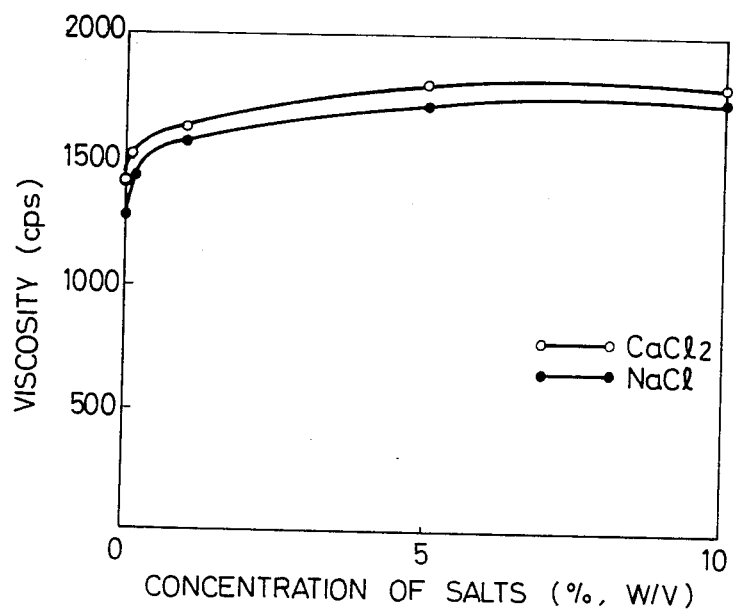
FIG. 5 is a graph showing the relationship between viscosity and concentration of the salts $CaCl_2$ and NaCl in 1% aqueous solution of AM-2.

The effect of calcium chloride and sodium chloride, respectively, on the viscosity of the 1% (w/v) aqueous solution is shown in FIG. 5. AM-2 is stable against divalent and monovalent cations.

Figure 6:
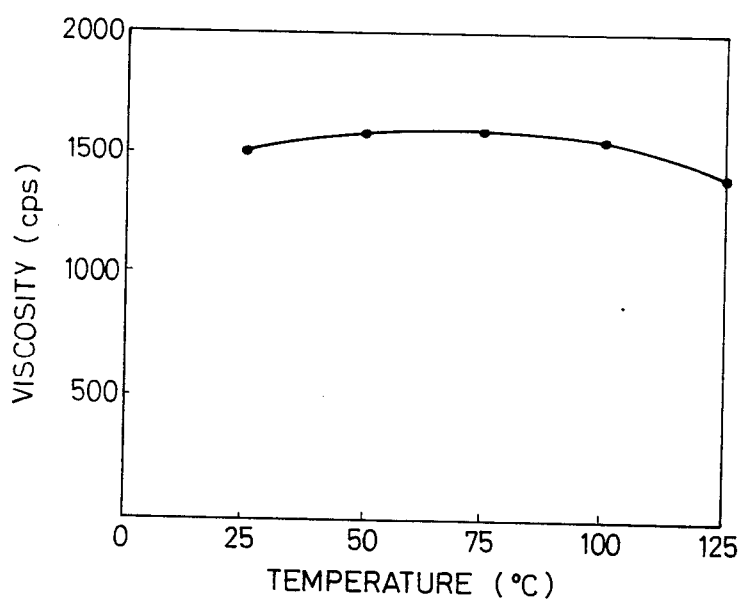
FIG. 6 is a graph showing the relationship between the viscosity and temperature of 1% aqueous solution of AM-2.

The effect of temperature on the viscosity of the 1% (w/v) aqueous solution is shown in FIG. 6. No significant changes in viscosity are observed up to 120° C.

7. Elemental analysis

C: 39.9±1%; H: 6.2±1%; N: 0%; ash: 3.0±1%.

8. Specific rotation $[\alpha]_D^{27} = 0 \sim +20$ (C=0.33, in aqueous solution)

9. Molecular weight

The average molecular weight measured by meniscus depletion method with an analytical ultracentrifuge is about $2.1 \times 10^6$. The average weight determined with a high performance liquid chromatograph (manufactured by Toyo Soda Mfg. Co., Ltd.) using pullulan (manufactured by Hayashibara Co., Ltd.) as a standard is $1 \times 10^6$ to $2 \times 10^6$. Accordingly, the molecular weight is about $10^5$ or above.

10. Melting point

AM-2 turns dark brown at 190° C. and decomposes at 250° C.

11. Nuclear magnetic resonance spectrum

Figure 7:
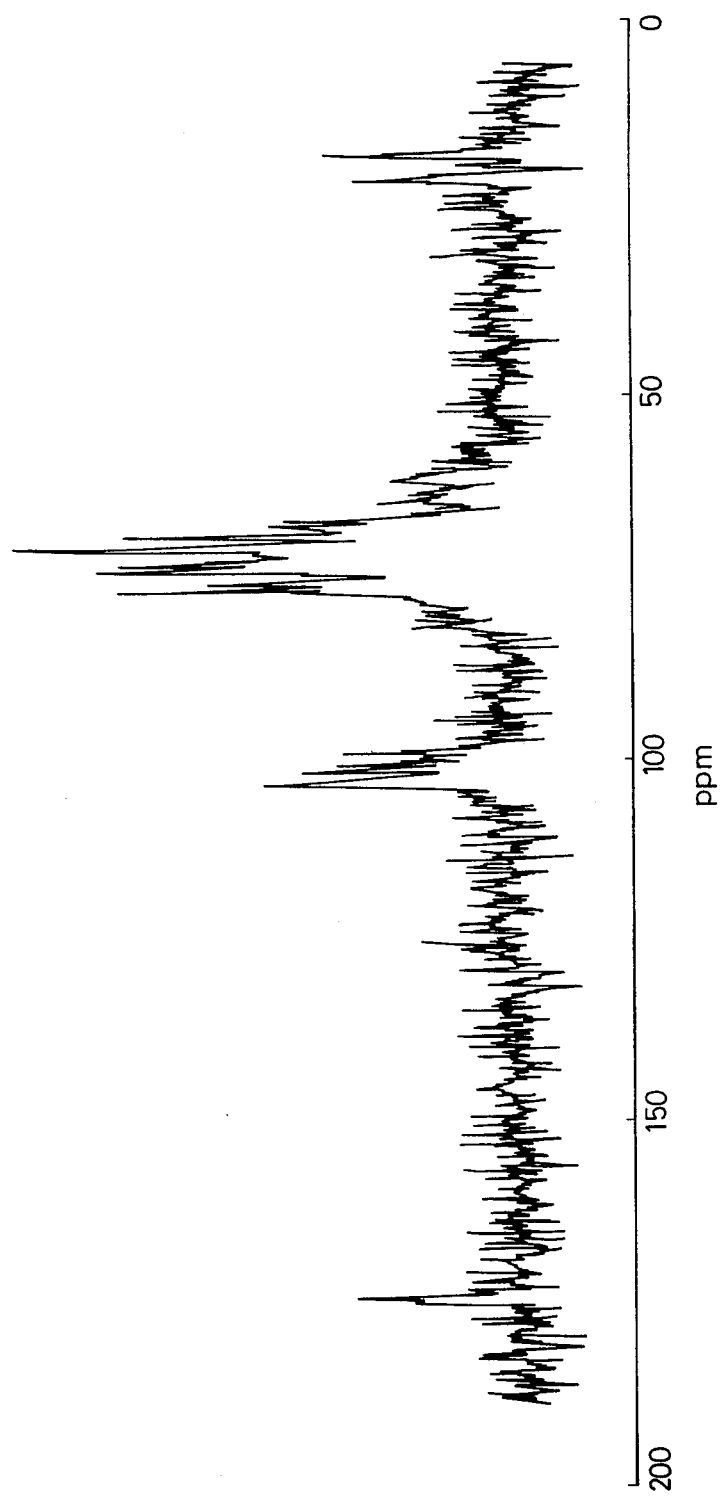
FIG. 7 shows the $^{13}$C-nuclear magnetic resonance spectrum of AM-2.

The $^{13}$C-nuclear magnetic resonance spectrum (solvent: D$_2$O; tube: 10 mm; internal reference: dioxane) is shown in FIG. 7. Main peaks are present at 174.2, 103.5, 101.5, 76.6, 75.9, 73.3, 70.9, 69.5, 61.4, 21.2, and 17.6 ppm.

12. The structure of the main repeating units of AM-2 is as follows:

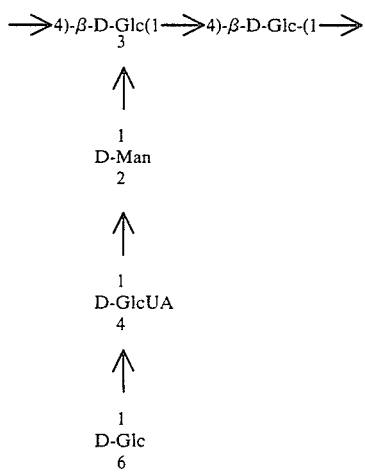

-continued

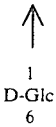  + OAc

1
D-Glc
6

1
L-Rha

Notes:
Glc: glucose
Rha: rhamnose
Man: mannose
GlcUA: glucuronic acid
OAc: O—acetyl group It is clear that AM-2 is a novel polysaccharide. It is entirely different from the heteropolysaccharide S-88 produced by a species of genus Pseudomonas (Japanese Patent Laid-Open No. 45902/1981, British Pat. No. 2,058,106) and the heteropolysaccharide S-130 produced by a species of genus Alcaligenes (Japanese Patent Laid-Open No. 45901/1981, British Pat. No. 2,058,107) in the ratio of components as shown below.

(1) Heteropolysaccharide S-88 (British Pat. No. 2,058,106) Glc:Rha:Man:GlcUA:Acetyl = 30~40:35~45:10~30:10~20:3~7 (%).

(2) Heteropolysaccharide S-130 (British Pat. No. 2,058,107) Glc:Rha:Man:GlcUA:Acetyl = 20~40:30~60:10~25:10~20:3~5 (%).

AM-2 is a novel and highly viscous polysaccharide produced by acetic acid bacteria which have been used for the brewing of vinegar from prehistoric times and whose safety has been historically confirmed. Because of its safety and high viscosity, AM-2 has excellent utility as an adhesive, coating agent, drilling mud additive and enhanced oil recovering agent, as well as a material for the production of foods, drugs and cosmetics. AM-2 can be produced by culturing AM-2 producing bacteria in a suitable culture medium.

As an AM-2-producing strain, any native strain, and variants thereof, can be used so far as these strains have the ability of producing AM-2.

An example of such strains is Acetobacter MH-1597 which belongs to genus Acetobacter and is newly isolated from vinegar mash by the present inventors. This strain has been deposited as FERM BP-280 with the Fermentation Research Institute of the Agency of Industrial Science and Technology, Japan.

Experiments concerning bacterial properties were conducted according to the methods of T. Hasegawa, "Classification and Identification of Microorganisms" (the University of Tokyo Press, June 20, 1975); "The Flagellation and Taxonomy of Genera Gluconobacter and Acetobacter with Reference to the Existence of Intermediate Strains" in the *Journal of General and Applied Microbiology*, Vol. 10, No. 2, pp. 95-126 (1964); and "Methods for Identifying Acetic Acid Bacteria" in "Identification Methods for Microbiologists", pp. 1-8 (1968) of the Society for Applied Bacteriology—Technical Series No. 2.

The yeast extract-glucose-agar medium was prepared by dissolving 5 g of yeast extract, 30 g of glucose, 3 g of polypeptone and 15 g of agar in 1 liter of distilled water and adjusting the pH to 6.5. The yeast extract-glucose-agar medium containing calcium carbonate was prepared by dissolving 5 g of yeast extract, 30 g of glucose, 3 g of polypeptone, 20 g of calcium carbonate and 15 g of agar in 1 liter of distilled water. The yeast extract-glucose liquid medium containing acetic acid and ethanol was prepared by dissolving 5 g of yeast extract, 30 g of glucose, 3 g of polypeptone and 2 g of acetic acid in 1 liter of distilled water, sterilizing the resulting solution, and then adding 3% (v/v) of ethanol. The MY-gelatin medium was prepared by dissolving 10 g of glucose, 5 g of polypeptone, 3 g of yeast extract, 3 g of malt extract and 200 g of gelatin in 1 liter of distilled water and adjusting the pH of 6.5. The bouillon liquid medium was prepared by dissolving 10 g of meat extract and 10 g of polypeptone in 1 liter of distilled water and adjusting the pH to 6.5. The bouillon liquid medium containing glucose was prepared by dissolving 10 g of glucose, 10 g of meat extract and 10 g of polypeptone in 1 liter of distilled water and adjusting the pH to 6.5.

The identification of ubiquinone was performed by paper chromatography, thin-layer chromatography, infrared and ultraviolet spectra and mass spectrometry.

I. Morphological characteristics
Shape: rod
Size: $0.6 \sim 0.7 \times 1.0 \sim 1.8$ $\mu$m
Population: single or pair, rarely in chain
Motility: none
Spore: none
Gram staining: negative
Acid-fastness: negative II. Cultural characteristics
1. Plate culture using the yeast extract-glucose-agar medium (cultured at 30° C. for 5 days)
Shape: circular
Edge: smooth and entire
Projection: capitate
Gloss: lustrous
Surface: smooth
Color tone: light brown and lustrous
2. Slant culture using the yeast extract-glucose-agar medium containing calcium carbonate (cultured at 30° C. for 3 days)
Growth: good
Projection: moderate
Surface: smooth
Color tone: light brown and lustrous
3. Static culture using the yeast extract-glucose liquid medium containing acetic acid and ethanol (cultured at 30° C. for 5 days).
Scant growth. Growth in a ring-like form. Broth was clear.
4. Static culture using the bouillon liquid medium (cultured at 30° C. for 7 days).
Scant growth. Growth in a ring-like form.
5. Static culture using the bouillon liquid medium containing glucose (cultured at 30° C. for 7 days)
Scant growth. Growth in a ring-like form.
6. Culture using the MY gelatin medium (cultured at 20° C. for 7 days.
Fair growth and no liquefaction.
7. Litmus milk medium (cultured at 30° C. for 7 days)
No coagulation III. Physiological characteristics
1. Nitrate reaction: negative
2. Denitrification: negative
3. VP test: negative
4. Formation of indole: negative
5. Formation of hydrogen sulfide: negative
6. Hydrolysis of starch: negative
7. Utilization of citric acid: negative in Christensen's medium
8. Utilization of inorganic nitrogen sources
Nitrates: negative
Ammonium salts: negative
9. Formation of pigment into medium: negative
10. Urease: negative
Oxidase: negative
11. Catalase: positive
12. Growth pH: $3.5 \sim 7.5$
Optimum pH: $5.0 \sim 6.5$
13. Growth temperature: $17° \sim 37°$ C.
Optimum temperature: $28° \sim 32°$ C.
14. Oxygen requirement: aerobic
15. Formation of 5-ketogluconic acid: positive
16. Formation of 2-ketogluconic acid: positive
17. Formation of 2,5-diketogluconic acid: negative
18. Formation of dihydroxyacetone: positive
19. Assimilation of ethanol: positive
20. Assimilation of acetic acid: positive
21. Assimilation of lactic acid: positive
22. Vitamin requirement: positive
23. Decomposition of acetate: positive
24. Decomposition of lactate: positive
25. Ferric chloride reaction:
negative (glucose broth)
negative (fructose broth)
26. Growth in Hoyer-Frateur-ethanol medium (vitamin added): negative
27. Growth in Hoyer-Frateur-glucose medium (vitamin added): positive IV. Assimilation of carbon sources and formation of acids and gases.
The results are given in Table 1.

TABLE 1

| Carbon sources | Assimilation | Formation of acids | Formation of gases |
|---|---|---|---|
| L-Arabinose | + | + | − |
| D-Xylose | + | + | − |
| D-Glucose | + | + | − |
| D-Mannose | + | + | − |
| D-Fructose | + | − | − |
| D-Galactose | + | + | − |
| Maltose | − | − | − |
| Sucrose | + | ± | − |
| Lactose | − | − | − |
| Trehalose | + | + | − |
| D-Sorbitol | ± | − | − |
| D-Mannitol | + | ± | − |
| Inositol | + | ± | − |
| Glycerol | + | + | − |
| Starch | − | − | − |
| Ethanol | + | + | − |
| Propanol | − | + | − |
| Butanol | − | + | − |
| Methanol | − | − | − |

Note:
+: assimilated or formed.
−: not assimilated or not formed.
±: slightly assimilated or formed.

V. Type of coenzyme in electron transfer system The main component of the coenzyme: ubiquinone-10

On the basis of the above characteristics, the taxonomic position of this bacterium was determined according to Bergey's Manual of Determinative Bacteriology, the 8th edition; "The Flagellation and Taxonomy of Genera Gluconobacter and Acetobacter with Reference to the Existence of Intermediate Strains" in the *Journal of General and Applied Microbiology*, vol. 10, pp. 95-126 (1964); and "Enzymatic Studies on the Oxidation of Sugar and Sugar Alcohol V. Ubiquinone of Acetic Acid Bacteria and its Relation to Classification of Genera Gluconobacter and Acetobacter, Especially of the So-Called Intermediate Strains" in the *Journal of General and Applied Microbiology*, vol. 15, pp. 181–196 (1969).

Acetobacter MH-1597 is a gram negative, aerobic, rod-shaped microorganism, oxidizes ethanol to acetic acid, and grows at pH 3.5. Thus, it is clear that this bacterium belongs to genus Acetobacter or genus Gluconobacter, which are generally referred to as acetic acid bacteria.

The bacterium of the present invention may be considered to belong to the genus Gluconobacter in that the main ubiquinone type is $Q_{10}$, vitamins are essential for growth and it is capable of forming dihydroxyacetone. However, it decomposes acetate and lactate. In this respect, it may be considered to belong to genus Acetobacter. Thus, it is very difficult to determine whether the bacterium of the present invention belongs to the genus Acetobacter or the genus Gluconobacter. In view of the fact, however, that the bacterium decomposes acetate and lactate and is capable of accumulating the above-mentioned novel AM-2 composed of glucose, rhamnose, mannose, glucuronic acid and acetyl group, it is believed reasonable to conclude that the present bacterium is a novel strain belonging to genus Acetobacter and has been named Acetobacter MH-1597.

Carbon sources which can be used in the present invention are glucose, galactose, fructose, sucrose, glycerol, mannitol, ethanol, citric acid, malic acid, molasses, saccharified solution of various grains containing starch, and mixtures thereof.

Nitrogen sources which can be used in the present invention include inorganic and organic nitrogen, such as yeast extract, peptone, corn steep liquor and ammonium sulfate.

Further, salts of potassium, calcium, magnesium, sodium, etc., and pantothenic acid, nicotinic acid, iron, cobalt and molybdenum, etc., can be effectively used for increasing the yield and the viscosity of AM-2.

The cultivation is performed at 20° C. to 35° C., preferably 28° C. to 32° C. in a medium with pH 3.5 to 7.5, preferably 5 to 7 under aerobic conditions, usually by shaking culture or aerated agitating culture. The culture period varies with various factors and is usually 24 to 120 hours.

AM-2 accumulated in a medium can be separated therefrom by conventional methods. For example, the culture solution, as such or after dilution with an appropriate amount of water, is subjected to centrifugal separation or filtration to remove the bacteria. A precipitant, such as methanol, ethanol, propanol, or acetone, etc., is added to the above obtained filtrate to precipitate fibrous AM-2, which is then washed with acetone and dried.

AM-2 is an acidic substance, therefore, AM-2 can also be obtained by adding, for example, cetyltrimethylammonium bromide to the culture solution freed from the bacterial cells.

The thus obtained crude AM-2 can be purified by conventional purification methods for polysaccharides. For example, the crude AM-2 is redissolved in water. After heat treatment, insoluble matter is completely removed by centrifugation. Then a precipitant such as acetone is added to the solution to reprecipitate AM-2. This operation is repeated to obtain white cottony AM-2 of high purity. Furthermore, precipitation with cetyltrimethylammonium bromide (CTAB treatment), dialysis, ion exchange resin treatment, etc., can be conducted to obtain a highly purified AM-2.

The following examples further illustrate the present invention.

EXAMPLE 1

In 1 liter of distilled water, 0.1 g of monopotassium phosphate, 0.25 g of magnesium sulfate heptahydrate, 0.005 g of ferric chloride, 2 g of yeast extract, 5 g of disodium citrate and 30 g of sucrose were dissolved to prepare a culture medium. In this way 3 liters of this medium were adjusted to pH 6.0, placed in a 5-liter jar fermentor and sterilized at 120° C. for 20 minutes.

The sterilized medium was inoculated with Acetobacter MH-1597 (FERM BP-280) which had been precultured in a Sakaguchi flask in a medium having the same composition as that of the above medium. Culture was conducted at 30° C. at an aerating rate of 0.5 VVM for 96 hours. After the completion of the culture, the pH of the culture solution was 7.8 and the viscosity was 5600 cps as measured with a Brookfield viscometer.

After the above culture, water was added to the culture solution to make its volume 10 liters. Centrifugal separation at 10,000 rpm was conducted for 20 minutes to remove the bacterial cells and solid matter. Then, 15 liters of ethanol was gradually added to the solution, whereby a white fibrous precipitation was formed. The precipitate was separated, washed with acetone and dried under vacuum. The yield of the thus obtained crude white fibrous AM-2 was 46.2 g (yield 25%).

Twenty two grams of the crude AM-2 was redissolved in 2 liters of water. Cetyltrimethylammonium bromide was added thereto to precipitate an AM-2-cetyltrimethyl-ammonium bromide complex. This complex was thoroughly washed with water and ethanol to remove an excess amount of cetyltrimethylammonium bromide. Then, a saturated aqueous sodium chloride solution was added to dissolve the complex. Three-fold amount of ethanol was added to the above solution to precipitate AM-2. The precipitate was separated, dried under vacuum, and redissolved in water. After the resulting solution was dialyzed in running water for three days, 3-fold amount of acetone was added to precipitate AM-2. The precipitate was recovered and dried under vacuum to obtain 18.5 g of purified AM-2.

EXAMPLE 2

In 1 liter of distilled water, 0.1 g of monopotassium phosphate, 0.1 g of dipotassium phosphate, 0.25 g of magnesium sulfate heptahydrate, 0.005 g of ferric chloride, 2 g of yeast extract, 5 g of sodium acetate and 25 g of sucrose were dissolved to prepare a culture medium. 3 liters of this medium was adjusted to pH 6.0, placed in a 5-liter jar fermentor, and sterilized at 120° C. for 20 minutes.

The sterilized medium was inoculated with Acetobacter MH-1597 (FERM BP-280) which had been precultured in a Sakaguchi flask by using a medium having the same composition as that of the above medium. Culture was conducted at 30° C. at an aerating rate of 0.5 VVM for 120 hours. After the completion of the culture, the pH of the culture solution was 8.6 and the viscosity was 5960 cps as measured with a Brookfield viscometer.

This culture solution was treated in the same manner as described in Example 1 to obtain 38 g (yield 50.7%) of crude AM-2.

EXAMPLE 3

In 1 liter of distilled water, 0.1 g of monopotassium phosphate, 0.1 g of dipotassium phosphate, 0.25 g of magnesium sulfate heptahydrate, 1 g of corn steep liquor, 5 g of sodium malate and 55 g of blackstrap molasses (having a sucrose content of 55%) were dissolved to prepare a culture medium. 10 liters of this medium was adjusted to pH 6.0, placed in a 20-liter jar fermentor, and sterilized at 120° C. for 20 minutes.

The sterilized medium was inoculated with Acetobacter MH-1597 (FERM BP-280) which had been precultured in a Sakaguchi flask by using a medium having the same composition as that of the above medium. Culture was conducted at 30° C. at an aerating rate of 0.5 VVM for 80 hours. During the culture, the pH of the medium was adjusted to about 6.0 with an aqueous solution of sodium hydroxide and hydrocholric acid. After the completion of the culture, the viscosity of the culture solution was 6400 cps as measured with a Brookfield viscometer.

This culture solution was treated in the same manner as described in Example 1 to obtain 187 g (yield 62%) of crude AM-2.

EXAMPLE 4

In 1 liter of distilled water, 1 g of monopotassium phosphate, 1 g of dipotassium phosphate, 0.25 g of magnesium sulfate heptahydrate, 2 g of corn steep liquor, 2 g of peptone, 5 g of sodium lactate and 20 g of glucose were dissolved to prepare a medium. 10 liters of this medium was adjusted to pH 6.0, placed in a 20-liter jar fermentor, and sterilized at 120° C. for 20 minutes.

The sterilized medium was inoculated with Acetobacter MH-1597 (FERM BP-280) which had been precultured in a Sakaguchi flask by using a medium having the same composition as that of the above medium. Culture was conducted at 30° C. at an aerating rate of 0.5 VVM for 80 hours. During the culture, the pH of the medium was adjusted to about 6.0 with an aqueous solution of sodium hydroxide and hydrochloric acid. After the completion of the culture, the viscosity of the culture solution was 4300 cps as measured with a Brookfield viscometer.

The culture solution was treated in the same manner as described in Example 1 to obtain 112 g (yield 56%) of crude AM-2.

EXAMPLE 5

In 1 liter of distilled water, 1 g of monopotassium phosphate, 1 g of dipotassium phosphate, 0.25 g of magnesium sulfate heptahydrate, 0.09 g of ferric chloride, 2 g of yeast extract, 5 g of sodium acetate and 30 g of glycerol were dissolved to prepare a culture medium. 3 liter of this medium was adjusted to a pH 6.0, placed in a 5-liter jar fermentor, and sterilized at 120° C. for 20 minutes.

The sterilized medium was inoculated with Acetobacter MH-1597 (FERM BP-280) which had been precultured in a Sakaguchi flask by using a medium having the same composition as that of the above medium. Culture was conducted at 28° C. at an aerating rate of 0.4 VVM for 96 hours. After the completion of the culture, the pH of the culture solution was 8.6 and the viscosity was 7400 cps as measured with a Brookfield viscometer.

The culture solution was treated in the same manner as described in Example 1 to obtain 63.4 g (yield 70.4%) of crude AM-2.

AM-2 is a highly viscous polysaccharide produced from acetic acid bacteria which have been used from prehistoric times for the production of vinegar and their safety has been confirmed. Its safety and high viscosity make AM-2 very useful as an additive, particularly as a thickening stabilizer in the food industry.

AM-2 can be added as a thickener or emulsion stabilizer in liquid and solid foods such as dressing, ice cream, jam, nectar, yogurt, chocolate, paste, sausage, syrup, jelly, cake, mayonnaise, whipping cream, catchup, sauce, soup, beer, alcoholic beverage, soy sauce, vinegar and pickles, etc.

The amount of AM-2 to be added to each food varies with the purpose of its use. Usually, AM-2 is added in an amount of 0.01 to 20% (w/v) based on the volume of a final product.

As conventional thickeners and emulsion stabilizers, vegetable polysaccharides such as locust bean gum, guar gum and pectin, algal polysaccharides such as carrageenan, agar and alginic acid, and microbial polysaccharides such as xanthan gum, pullulan and dextran are known.

However, vegetable and algal polysaccharides have disadvantages in that their outputs are greatly influenced by the weather and other factors and their supply tends to become irregular, because they are natuarlly occurring substances. Further, they have a disadvantage in stability, particularly resistance to acids and heat.

On the other hand, microbial polysaccharides have an advantage in that they can be constantly supplied. However, conventional microbial polysaccharides are produced by pathogenic microorganisms such as *Xanthomonas campestric* and *Pullularia pullulans,* so that they exert a dangerous effect on the environment when mass production is employed and have fundamentally a serious defect in their safety as food additives.

On the contrary, the safety of AM-2 has been historically assured. Further, AM-2 is excellently resistant to acids, heat, salts and pH, so that AM-2 is very useful as a thickener or an emulsion stabilizer for foods as compared with conventional polysaccharides.

The following descriptions further illustrate the usefulness of AM-2 of the present invention.

Heretofore, locust bean gum, guar gum, carrageenan and tragacanth gum have been used as stabilizers for a separation type dressing. But they have disadvantages in that they are unstable at low pH and hardly dissolved in cold water. On the other hand, AM-2 has excellent properties in that it is resistant to pH and salts and is soluble in cold water. Therefore, AM-2 is superior to the above conventional gums as a stabilizer for a separation type dressing. AM-2 is generally added in an amount of 0.05 to 1.0% (w/v) based on the volume of final product.

Heretofore, xanthan gum, carrageenan, guar gum and tragacanth gum have been used as thickening stabilizers for yogurt. But they have disadvantages in that they are bound to milk protein, particularly casein, to cause syneresis, and decrease in viscosity at low pH. On the other hand, AM-2 is very stable at low pH as stated above, does not bind to milk protein and does not cause syneresis at all. Thus, AM-2 is superior to the conventional gums as a stabilizer for yogurt. AM-2 is generally added in an amount of 0.05 to 2.0% (w/v) based on the volume of final product.

For example, each of AM-2 and xanthan gum was added to commercially available plain yogurt in an amount of 1.0% based on the volume of yogurt. The results of the preservation (4° C.) test are given in Table 2.

TABLE 2

| Days (4° C.) | Viscosity of the yogurt to which AM-2 has been added (cps) | Viscosity of the yogurt to which xanthan has been added (cps) |
| --- | --- | --- |
| 1 | 1830 | 1030 |
| 3 | 1960 | syneresis |
| 10 | 2020 | " |
| 30 | 1930 | " |
| 60 | 1950 | " |

It is apparent from Table 2 that the viscosity of the yogurt to which AM-2 has been added, is not reduced even after preservation of 60 days and the yogurt does not cause syneresis at all. On the other hand, the yogurt to which xanthan gum has been added causes syneresis after preservation for only 3 days.

AM-2 is also expected to be useful as a material for drugs such as immunoactivator, anti-hypercholesterolemia, anti-hypertensive and antidiabetic drugs, because of the safety and the high viscosity of AM-2. AM-2 is also applicable alone or in combination with one or more of known viscous polymers for industrial uses as a material for lubricants, coating agents, pastes, cosmetics and as a thickening agent in enhanced oil recovery.

It will be obvious to those skilled in the art that various changes may be made without departing from the scope of the invention and the invention is not be to considered limited to what is shown in the drawings and described in the specification.

What is claimed is:

1. Acidic heteropolysaccharide AM-2 having the following physiochemical characteristics:
    (1) composition
        composed of glucose, rhamnose, mannose, glucuronic acid and acetyl group as main components, the molar ratio of glucose:rhamnose:mannose:glucuronic acid being 4:0.9~1.1:0.9~1.1:0.9~1.1 and the acetyl group content is 4 to 8%;
    (2) infrared spectrum
        the infrared spectrum is as shown in FIG. 1;
    (3) color reaction
        Anthrone reaction: positive
        Carbazole reaction: positive
        Elson-Morgan's reaction: negative
        Iodine reaction: positive;
    (4) solubility in solvents
        soluble in water, and insoluble in ethanol, ether, acetone;
    (5) color and appearance
        the purified polysaccharide is white, cottony or fibrous;
    (6) viscosity
        the aqueous solution is colorless, transparent and viscous, and the viscosity of 1% solution is 1200 to 2000 cps as determined with a torque measuring viscometer at 25° C. and a rate of 30 rpm;
    (7) elemental analysis:
        C: 39.9±1%; H: 6.2±1%; N: 0%; ash: 3.0±1.0%;
    (8) Specific rotation
        $[\alpha]_D^{27} = 0 \sim +20$
        (C=0.33 in the aqueous solution);
    (9) molecular weight
        about $10^5$ or above;
    (10) melting point
        the polysaccharide turns dark brown at 190° C. and decomposes at 250° C.; and
    (11) nuclear magnetic resonance spectrum
        the $^{13}$C-nuclear magnetic resonance spectrum is as shown in FIG. 7.

* * * * *